United States Patent [19]

Shimamura et al.

[11] Patent Number: 4,911,907
[45] Date of Patent: Mar. 27, 1990

[54] COCKROACH ATTRACTANTS

[75] Inventors: Haruo Shimamura, Urawa; Kimihide Shimano, Ageo; Tatsuoki Iguchi, Satte; Hiroshi Yamaguchi, Tokyo, all of Japan

[73] Assignee: Taisho Pharmaceutical Co., Ltd., Japan

[21] Appl. No.: 103,296

[22] Filed: Oct. 1, 1987

[30] Foreign Application Priority Data

Oct. 14, 1986 [JP] Japan .................................. 61-243568

[51] Int. Cl.$^4$ ............................................ A01N 25/00
[52] U.S. Cl. ...................................... 424/84; 514/646; 514/731
[58] Field of Search ............................................ 424/84

[56] References Cited

U.S. PATENT DOCUMENTS 4,219,570  8/1980  Inazuka et al. ...................... 424/343

FOREIGN PATENT DOCUMENTS

| 19-320   | 1/1944  | Japan . |         |
|----------|---------|---------|---------|
| 0118524  | 10/1978 | Japan   | 424/84  |
| 0121935  | 10/1978 | Japan   | 424/84  |
| 56-29502 | 3/1981  | Japan . |         |
| 56-30905 | 3/1981  | Japan . |         |
| 56-30940 | 3/1981  | Japan . |         |
| 56-79602 | 6/1981  | Japan . |         |
| 56-79640 | 6/1981  | Japan . |         |
| 56-87536 | 7/1981  | Japan . |         |
| 0067209  | 4/1984  | Japan   | 424/84  |
| 61-69701 | 4/1986  | Japan . |         |
| 61-72702 | 4/1986  | Japan . |         |
| 1069701  | 4/1986  | Japan   | 424/84  |

OTHER PUBLICATIONS

"Bioassay Procedure of Sex Stimulant of the American Cockroach" Shozo Takashi and Chikayoshi Kitamura Mar. 16, 1972, pp. 133–140.

Primary Examiner—Leonard Schenkman
Attorney, Agent, or Firm—Lorusso & Loud

[57]    ABSTRACT

Cockroach attractants comprising as an active ingredient an alkylphenol or an alkylphenylamine are provided. The cockroach attractants exhibit strong attracting activity, even when used alone, specifically for male cockroaches, with a good stationing effect. The activity does not go down even when the male and female cockroaches live together.

8 Claims, No Drawings

COCKROACH ATTRACTANTS

BACKGROUND OF THE INVENTION

1. Field of the Invention

The present invention relates to attractants for cockroaches.

Methods for exterminating cockroaches known in the art include, one using tackiness plate in a trap and the other one using toxic baits.

The effects achieved by such prior art are expected to be enhanced by a simultaneous use of an attractant, as is achieved by the present invention as will be described hereinafter.

2. Description of the Prior Art

*Periplaneta americana* L., *Periplaneta fuliginosa* S. and *Periplaneta japonica* K. are species of cockroaches that are most known and widely distributed in Japan as the house cockroach.

There have been known as the attractant for cockroaches sex pheromons obtained by extraction from the feces and the midgut of cockroaches. Also known are certain monoterpenoids as disclosed in Japanese Patent Laid-Open-to-Public (L-O-P) Nos. 56-29502, 56-30905, 56-30940, 56-79602, 56-79640 and 56-87536; fatty acids such as myristic acid and palmitic acid and esters of these fatty acids as disclosed in Japanese Patent Publication No. 44-320; and naphthalene derivatives as disclosed in Japanese Patent L-O-P Nos. 61-69701 and 61-72702.

Extraction of the sex pheromones, however, requires a large number of cockroaches. Moreover, since the sex pheromones are of excitable nature, cockroaches do not necessarily settle down with them. Furthermore, the activities tend to go down markedly when male and female cockroaches live together, as reported in Appl. Ent. Zool, 2 (3), pp. 133 (1972).

On the other hand, monoterpenoids require complicated synthetic procedures in order to obtain them.

With fatty acids such as myristic acid and palmitic acid and esters of these fatty acids, only somewhat weak attracting effect is brought about. Further, they produce no stationing or ingestion-stimulating effect when they are used alone, and therefore, addition of starch or sugars is required.

The prior art methods thus necessitate high production cost, associated with somewhat bulky size of the attractants which is inconvenient in use.

DETAILED DESCRIPTION OF THE INVENTION

As a result of extensive studies in pursuit of effective cockroach attractants that would overcome the disadvantages involved in the prior arts as noted above, the present inventors have found that the compounds represented by the following formula (I) exhibit strong attracting activity, even when used alone, specifically for male cockroaches, with a good stationing effect and that the activity does not go down even when the male and female cockroaches live together.

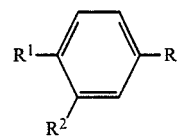

wherein, $R^1$ represents a straight or branched chain alkyl group having from 3 to 7 carbon atoms; $R^2$ represents a hydrogen atom or a methyl group; and R represents a hydroxy group or an amino group.

The present invention, therefore, is concerned with cockroach attractants that contain as an active ingredient one or more compounds represented by the formula (I).

Representative examples of the compounds of the formula (I) are given in the following Table 1.

TABLE 1

| Compound | R | $R^1$ | $R^2$ |
|---|---|---|---|
| 3-Methyl-4-isopropylphenol | OH | iso-$C_3H_7$ | $CH_3$ |
| p-n-Butylphenol | OH | n-$C_4H_9$ | H |
| p-sec-Butylphenol | OH | sec-$C_4H_9$ | H |
| p-tert-Butylphenol | OH | tert-$C_4H_9$ | H |
| p-n-Amylphenol | OH | n-$C_5H_{11}$ | H |
| p-tert-Amylphenol | OH | tert-$C_5H_{11}$ | H |
| p-n-Butylaniline | $NH_2$ | n-$C_4H_9$ | H |
| p-n-Amylaniline | $NH_2$ | n-$C_5H_{11}$ | H |
| p-n-Hexylaniline | $NH_2$ | n-$C_6H_{13}$ | H |

The compounds represented by the formula (I) and a process for the preparation thereof are known per se in the art.

The cockroach attractants of the invention may be prepared, for example, by the following manner:

One or more compounds in Table 1 are dissolved in a suitable solvent (for example, a hydrophilic organic solvent such as acetone, methanol, ethanol, tetrahydrofuran, ethylene glycol, diethylene glycol or dimethylformamide, or a lipophilic organic solvent such as benzene, chloroform, diethyl ether, methylene chloride or n-hexane), then the solution is impregnated in a suitable carrier such as filter paper, cardboard, unwoven cloth, cotton cloth or flannel, and finally the carrier containing the solution is dried.

Alternatively, the cockroach attractants may be formulated into various forms such as oil preparation, emulsifiable concentrate, wettable powder, powder, granule, pill, tablet, aerosol or the like, employing one or more of the compounds shown in Table 1 above in admixture with suitable auxiliary agents known per se such as emulsifier, dispersing agent, suspending agent, wetting agent, spreading agent, excipient, stabilizer or the like.

The cockroach attractants according to the invention contains the compound of the formula (I) usually in an amount of from 0.1 to 20.0%, preferably from 0.5 to 5.0% by weight.

The cockroach attractants of the invention exhibit a specific attracting activity and achieve a remarkable cockroach controlling effect.

As described above, the compounds of the formula (I) show the attracting activity, even when used alone, with a good stationing effect. Therefore, there is no need for the addition of starch or sugars upon preparation of the cockroach attractants. This brings about low production cost and minimize the size of such attractants.

The cockroach control may be achieved by placing the cockroach attractant of the invention on a tackiness plate or by mixing it with a toxic bait.

The present invention will be described in more detail by the following Examples and Experiments.

EXAMPLE 1

2.0 g Of p-n-amylphenol were added to about 200 ml of n-hexane, then the mixture was stirred mechanically for 10 minutes to give a solution. 10 ml Of the solution were uniformly impregnated into an unwoven cloth of 20 cm width, 50 m length and 0.1 cm thickness, then the cloth was dried in air to evaporate the n-hexane. The cloth was then cut into tapes of 0.5 cm width and 20 cm length. These tapes may be mounted at the center of a tackiness plate of receptacl-shaped cockroach trap.

n-Butylaniline and other compounds listed in Table 1 were treated in the same manner as above to give attracting tapes.

EXAMPLE 2

A mixture of 4.0 g of 3-methyl-4-isopropylphenol, 20 g of white petrolatum and 76 g of permethrin was coated on a polyethylene tape of 5 cm width and 200 m length, which was then cut into insecticidal tapes of 20 cm length.

EXAMPLE 3

A mixture of 2 g of p-n-butylaniline, 22 g of white petrolatum and 76 g of permethrin was coated on a polyethylene tape of 5 cm width and 200 m length, which was then cut into insecticidal tapes of 20 cm length.

EXAMPLE 4

4 g Of p-n-amylphenol were added to about 200 ml of acetone and the mixture was vigorously shaken to make a solution. 0.1 ml Of the solution was impregnated with a pipette in a round filter paper (Toyo Filter Paper No. 2), which was then dried thoroughly in air until the acetone was completely evaporated.

A sheet of the impregnated filter paper was placed in a glass cylinder of 13 cm diameter and 18 cm height, upper inside of which had been previously coated with petrolatum with 5 cm width, to give a simple cockroach trap.

EXAMPLE 5

3 g Of p-n-amylphenol and 5 g of p-n-butylphenol were added to about 400 ml of acetone and the mixture was vigorously shaken to make a solution. 0.1 ml Of the solution was impregnated with a pipette in a round filter paper (Toyo Filter Paper No. 2 ), which was then dried thoroughly in air until the acetone was completely evaporated. A sheet of the impregnated filter paper was placed in a glass cylinder of 13 cm diameter and 18 cm height, upper inside of which had been previously coated with petrolatum with 5 cm width, to give a simple cockroach trap.

n-Butylaniline and other compounds listed in Table 1 were treated in a similar manner as above to give attractant tapes.

EXAMPLE 6

A mixture of 10 g of p-n-hexylaniline, 200 g of natural rubber, 780 g of a tackifier agent and 10 g of an antioxidant was thoroughly kneaded to give a compound. 3.6 g Of the compound were coated on a cardboard of 9 cm width and 20 cm length to give a tackiness plate to be used for receptacle-shaped cockroach traps.

EXPERIMENT 1

*Periplaneta americana* L., *Periplaneta fuliginosa* S. and *Periplaneta japonica* K., each group consisting of 100 adult males and females (1:1) of one month old after adult emergence, were used as the test insects. Compounds listed in Table 1 were used as the test compounds. Two circles, each 3.5 cm$^2$, were drawn on a filter paper of 11 cm diameter (Toyo Filter Paper No. 2) at equal distances. A solution containing 1000 μg of one of the test compounds was applied to one circle, while 20 μg of acetone were applied to the other circle. The filter paper was thoroughly dried in air to give a test sheet. A group of the each test cockroaches were placed in a transparent polycarbonate cage (35×30×18 cm) and they were reared under the conditions of 25° C. and 12L-12D (12 hours light period and 12 hours dark period) for fitting themselves in the cage. The test sheet was then placed in each of the cages and, after 24 hours, the sheets were recovered to examine the degree of attraction. The test compounds exhibit attracting activity for all three species, in particular strongly for *Periplaneta americana* L. The results are shown in Table 2.

TABLE 2

| Compound | A | B | C |
| --- | --- | --- | --- |
| 3-Methyl-4-isopropylphenol | +++ | + | + |
| p-n-Butylphenol | +++ | + | ++ |
| p-sec-Butylphenol | +++ | +− | + |
| p-tert-Butylphenol | +++ | +− | + |
| p-n-Amylphenol | +++ | + | + |
| p-tert-Amylphenol | +++ | + | ++ |
| p-n-Butylaniline | +++ | + | ++ |
| p-n-Amylaniline | +++ | + | ++ |
| p-n-Hexylaniline | +++ | + | + |

Remarks:
A : *P. ameriana* L.
B : *P. fuliginosa* S.
C : *P. japonica* K.
+++ : Marks of very vigorous eating
++ : Marks of vigorous eating
+: 4–10 Marks of eating
+− : 2–3 Marks of eating

EXPERIMENT 2

60 Adult male cockroaches (*P. americana* L. ) of one month old after adult emergence were placed in a room having the floor space of about 20 m$^2$ and they were given plenty of feed and water for a week. Three set of traps, two per set, were placed on the floor circularly, one meter away from the center of the room.

The traps used are ones disclosed in Japanese Utility Model L-O-P No. 54-142679. A round filter paper of 3.5 cm$^2$ was placed at the center of tackiness face of each of the traps. The filter papers of traps A contained 80 μg of p-n-butylphenol that had been impregnated. The filter papers of traps B contained 2000 μg of ar-α-tetralol described in Japanese Patent L-O-P No. 61-72702. The filter papers of traps C contained no active compound. The number of cockroaches caught in each trap was counted after 24 hours and the results are shown in Table 3.

TABLE 3

|  | Trap A | Trap B | Trap C |
|---|---|---|---|
| Number of cockroaches | 22 | 18 | 6 |

What is claimed is:

1. A composition for exterminating cockroaches which comprises an amount effective to attract cockroaches of one or more compounds selected from the group consisting of:
   3-methyl-4-isopropylphenol,
   p-n-butylphenol,
   p-sec-butylphenol,
   p-tert-butylphenol,
   p-n-amylphenol,
   p-tert-amylphenol,
   p-n-butylaniline,
   p-n-amylaniline and
   p-n-hexylaniline;
and, in admixture with said compound, a poison toxic to said cockroaches.

2. A composition as claimed in claim 1 formulated into an oil preparation, emulsifiable concentrate, wettable powder, powder, granule, pill, tablet or aerosol.

3. A composition as claimed in claim 2 which contains one or more compounds in the total amount of from 0.1% to 20.0% by weight.

4. A composition as claimed in claim 1 impregnated, with the aid of a solvent, in a filter paper, cardboard, unwoven cloth, cotton cloth or flannel.

5. A method of attracting *Periplaneta americana* L. cockroaches comprising applying a composition containing one or more compounds selected from the group consisting of:
   3-methyl-4-isopropylphenol,
   p-n-butylphenol,
   p-sec-butylphenol,
   p-tert-butylphenol,
   p-n-amylphenol,
   p-tert-amylphenol,
   p-n-butylaniline,
   p-n-amylaniline and
   p-n-hexylaniline;
in a location wherein said cockroaches are present in the environment, whereby said cockroaches are attracted to said compound.

6. The method of claim 5, wherein said composition is applied in a trap for said cockroaches.

7. The method of claim 5, wherein said composition further comprises a component which is toxic to said cockroaches.

8. A cockroach trap comprising a tacky surface for capturing cockroaches and, for attracting cockroaches to said tacky surface, one or more compounds selected from the group consisting of:
   3-methyl-4-isopropylphenol,
   p-n-butylphenol,
   p-sec-butylphenol,
   p-tert-butylphenol,
   p-n-amylphenol,
   p-tert-amylphenol,
   p-n-butylaniline,
   p-n-amylaniline and
   p-n-hexylaniline.

* * * * *